United States Patent
Andersson (10) Patent No.: US 6,844,004 B2
(45) Date of Patent: Jan. 18, 2005

(54) TOPICAL FORMULATIONS OF NATAMYCIN/PIMARICIN

(75) Inventor: Borje S. Andersson, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/294,491

(22) Filed: Nov. 14, 2002

(65) Prior Publication Data

US 2003/0129225 A1 Jul. 10, 2003

Related U.S. Application Data

(63) Continuation-in-part of application No. 09/415,890, filed on Oct. 8, 1999, which is a continuation of application No. 08/911,607, filed on Aug. 15, 1997, now Pat. No. 6,045,815
(60) Provisional application No. 60/332,806, filed on Nov. 14, 2001.

(51) Int. Cl.[7] .......................... A61K 9/10; A61K 31/70; A61K 31/7048; A01N 25/00; A01N 25/02
(52) U.S. Cl. ..................... 424/405; 424/400; 424/70.1; 514/31
(58) Field of Search ............................... 424/400, 405, 424/70.1; 514/31

(56) References Cited

U.S. PATENT DOCUMENTS

| | | |
|---|---|---|
| 3,343,958 A | 9/1967 | Morse |
| 3,343,968 A | 9/1967 | Huhtanen |
| 3,892,850 A | 7/1975 | Struyk et al. ............... 424/119 |
| 4,148,891 A | 4/1979 | Smink ........................ 424/181 |
| 4,536,494 A | 8/1985 | Carter .......................... 514/31 |
| 4,600,706 A | 7/1986 | Carter .......................... 514/31 |
| 4,766,046 A | 8/1988 | Abra et al. .................. 424/450 |
| 4,794,117 A | 12/1988 | Corbiere ...................... 514/420 |
| 4,883,785 A | 11/1989 | Chow et al. .................. 514/31 |
| 4,950,477 A | 8/1990 | Schmitt et al. ................ 424/43 |
| 5,006,595 A | 4/1991 | Smith et al. ................. 524/548 |
| 5,277,914 A | 1/1994 | Szoka, Jr. .................... 424/450 |
| 5,430,057 A | 7/1995 | Andersson et al. ......... 514/517 |
| 5,552,151 A | 9/1996 | Noordam et al. ........... 424/439 |
| 5,559,148 A | 9/1996 | Andersson et al. ......... 514/517 |
| 5,651,991 A | 7/1997 | Sugiyama .................... 424/502 |
| 5,821,233 A | 10/1998 | Van Rijn et al. ............. 514/31 |
| 5,858,410 A * | 1/1999 | Muller et al. ................ 424/489 |
| 5,877,205 A | 3/1999 | Andersson ................... 514/449 |
| 6,045,815 A * | 4/2000 | Andersson et al. ......... 424/405 |
| 6,107,333 A | 8/2000 | Andersson .................... 514/449 |
| 6,239,113 B1 * | 5/2001 | Dawson et al. ............... 514/29 |
| 6,291,500 B2 | 9/2001 | Ponikau ....................... 514/393 |
| 6,369,036 B1 | 4/2002 | Van Rijn et al. ............. 514/31 |
| 6,406,713 B1 * | 6/2002 | Janoff et al. ................. 424/450 |
| 2002/0177562 A1 | 11/2002 | Weickert et al. .............. 514/27 |

FOREIGN PATENT DOCUMENTS

| | | |
|---|---|---|
| DE | 3819504 | 12/1989 |
| EP | 0664130 | 7/1995 |
| GB | 2106498 | 4/1983 |
| GB | 2116425 | 9/1983 |
| WO | WO 93/07884 | 4/1993 |
| WO | WO 96/29998 | 10/1996 |

OTHER PUBLICATIONS

Hansen et al., "Re-examination and further development of a precise and rapid dye method for measuring cell growth/cell kill," *J. Immunol. Methods*, 119:203–210, 1989.

(List continued on next page.)

*Primary Examiner*—Thurman K. Page
(74) *Attorney, Agent, or Firm*—Fulbright & Jaworski, LLP (57) ABSTRACT

The present invention relates to formulations of Pimaricin (also called Natamycin), that are useful for the treatment and suppression of topical infections such as those caused by various pathogens including molds and yeast, that are resistant to azole compounds and to Amphotericin B. Methods for treatment of infections are also set forth.

20 Claims, 1 Drawing Sheet

OTHER PUBLICATIONS

Korteweg et al., "Some pharmacological properties of Pimaricin and possible clinical application of this antifungal antibiotic," *IInd int. Symp. Chemotherapy*, 11:261–272, 1963.

Lavingia and Dave, "Comparative study of amphotericin B Pimaricin and Gentian violet on ocular fungi," *Indian J. Ophalmol.*, 34:73–77, 1986.

Masterton et al., "Natamycin in genital candidosis in men," *Br. J. Vener. Dis.*, 51(3):210–212, 1975.

Mulligan and McCauley, "Factors that influence the determination of residual solvents in pharmaceuticals by automated static headspace sampling coupled to capillary GC–MS," *J. Chromatogr. Sci.*, 33:49–54, 1995.

Raab, "Natamycin (Pimaricin) its properties and Possibilities in medicine," 1–134, Georg Thieme Publishers Stuttgart, 1972.

Sawyer et al., "Miconazole: a review of its antifungal activity and therapeutic efficacy," *Drugs*, 9(6):406–423, 1975.

Shah et al., "Microsphaeropsis olivacea keratitis and consecutive endophthalmitis," *Am. J. of Ophthalmology*, 131:142–143, 2001.

Spiegel and Noseworthy, "Use of nonaqueous solvents in parental products," *J. Pharm. Sci.*, 52:917–927, 1963.

Struyk et al., "Pimaricin, a new antifungal antibiotic," *Antibiot. Ann.*, 878–885, 1957–1958.

Yalkowsky and Roseman, "Solubilization of drugs by cosolvents," In: *Techniques of solubilization of drugs*, Yalkowsky (Ed.), 91–134, Marcel Dekker Inc., NY, NY, 1981.

Anaissie et al., "Emerging fungal pathogens," *Eur. J. Clin. Microbiol. Infect. Dis.*, 8:323–330, 1989.

Anaissie et al., "Fluconazole susceptibility testing of *Candida albicans*: microtiter method that is independent of inoculum size, temperature, and time of reading," *Antimicrob. Methods Chemother.*, 35:1641–1646, 1991.

Andersson et al., "KBM–7, a human myeloid leukemia cell line with double Philadelphia chromosomes lacking normal c–ABL and BCR transcripts," *Leukemia*, 9:2100–2108, 1995.

Andersson et al., "Nucleotide excision repair genes as determinants of cellular sensitivity to cyclophosphamide analogs," *Cancer Chemother. and Pharmacol.*, 38:406–416, 1996.

Andersson et al., "Ph–positive chronic myeloid leukemia with near–haploid conversion in vivo and establishment of a continuously growing cell line with similar cytogenetic pattern," *Cancer Genetics and Cytogenet.*, 24:335–343, 1987.

Christensen and Bush, "Vaginal *candida albicans* treated with three different concentrations of natamycin (Pimafucin) for 6 days," *Acta Obstet Gynecol Scand*, 61:325–328, 1982.

Drug Facts and Comparisons, Wolters Kluwer Co., St. Louis, MO, Intravenous Nutritional Therapy, p. 138, 1977.

Drug Information for Health Care Professional: USPDI–Natamycin, p. 1705, 1989.

Gallagher et al., "Characterization of the continuous differentiation myeloid cell line (HL–60) from a patient with acute promyelocytic leukemia," *Blood*, 54:713–73, 1979.

Kajda, "Local treatment of chronic paranoychia with pimaricin–dimethyl–sulfoxide (DMSO) suspension," Abstract No. 35097, Chemical Abstracts, 79:No. 6, Columbus, Ohio, 1973.

* cited by examiner

Fig. 1

TOPICAL FORMULATIONS OF NATAMYCIN/PIMARICIN

BACKGROUND OF THE INVENTION

The present application claims priority to co-pending U.S. patent application Ser. No. 60/332,806, filed Nov. 14, 2001, and is a continuation-in-part of U.S. Ser. No. 09/415,890, filed Oct. 8, 1999, which was a continuation of U.S. Ser. No. 08/911,607, filed Aug. 15, 1997, now U.S. Pat. No. 6,045,815. The entire text of the above-referenced provisional application disclosure is specifically incorporated by reference herein without disclaimer.

1. Field of the Invention

The present invention relates generally to the fields of infectious conditions and drug formulations. More particularly, it concerns the development of a pharmaceutical formulation of Pimaricin (also called as Natamycin) that can be used to treat and prevent a wide variety of topical infections caused by fungal and microbial pathogens.

2. Description of Related Art

Superficial fungal infections constitute one of the more difficult challenges for clinicians caring for patients with diabetes mellitus and/or immunocompromised states, such as those caused by cancer, cancer-therapy and HIV-infection (Anaissie et al., 1989). While the incidence of hematogenous candidiasis in immunocompromised patients has decreased significantly with the introduction of fluconazole, the occurrence of superficial opportunistic infections affecting the mucous membranes and the skin of immunocompromised patients and have persisted and pose a major clinical problem carrying also the risk of serving as an entry port for systemic infection. The most common of such infections is oral thrush and vaginal candida infections.

The use of either physician-prescribed or over the counter dispensed topical antifungal therapy for vaginal fungal infections appears to have increased gradually over the last decade. The indiscriminant use of azole compounds in this setting and its concomitant use as prophylaxis against systemic candida infection after cancer chemotherapy and in AIDS-patients has raised the incidence of resistance against such azole-based antifungal therapy.

The polyene antibiotic Amphotericin B (AMB), which typically is the first-line treatment for documented or suspected systemic mold infections, is associated with side effects such as substantial local toxicity and irritation. Furthermore, inflammation of the mucosal surface with which it comes in contact is seen in >75% of treated subjects. In addition, AMB is largely ineffective against Fusariosis.

Thus, an effective antimycotic agent with low local organ toxicity, broad antifungal spectrum activity, predictable lack of systemic absorption after topical administration and activity against both *Fusarium* spp. and *Aspergillus* spp. appears highly warranted.

Pimaricin, also called as Natamycin, is an effective antifungal agent, exerting significant activity against molds and yeast, particularly of the *Candida, Trichomonas, Aspergillus* and *Fusarium* species. Pimaricin is especially effective in molds and yeasts that are resistant to azole compounds and to Amphotericin B.

Pimaricin was first isolated in 1955 from a strain of Streptomyces (Struyk et al., 1957–1958). Pimaricin exhibited a wide range of in vitro activity against fungi, yeast, and trichomonads (Struyk et al., 1957–1958; Korteweg et al., 1963; Raab, 1972). The drug was found to have little or no toxicity after oral administration, being virtually non-absorbable from the gastrointestinal tract (Korteweg et al., 1963; Raab, 1972). In fact, pimaricin's prominent chemical stability, paired with its apparent lack of intestinal absorption and systemic toxicity, formed the basis for its FDA-approved use in the food industry, where it is used to prevent the proliferation of aflatoxin-producing molds (Code of Federal Regulations, Food and Drugs, 1995).

The lack of solubility of pimaricin in various solvents, both aqueous and organic, that are compatible for human administration severely restricted its use in clinical medicine. Past attempts to solubilize pimaricin in vehicles that are safe for intravascular administration in humans have all failed, despite the hard work by Stuyk and others (Struyk et al., 1957–1958; U.S. Pat. No. 3,892,850; Korteweg et al., 1963; Raab, 1972). Korteweg and coworkers attempted to solubilize the drug by mixing it with a complex polysaccharide (Korteweg et al., 1963). Although the water-solubility of this formulation increased dramatically, its antifungal in vitro activity decreased to about ⅓ of that of native Natamycin. Further, this preparation is comparatively toxic in experimental animals, and it was therefore deemed unsuitable for systemic parenteral administration in humans (Struyk et al., 1957–1958).

Other attempts to prepare pimaricin based creams for topical treatments of genital infections has resulted in formulations in which the pimaricin is present in a predominantly insoluble crystalline form (Christensen and Buch, 1982; WO 93/07884). Thus, attempts to solubilize Natamycin and make formulations that were applicable for topical application were unsuccessful and led to clinical trials that demonstrated that natamcyin was inferior to alternative drugs for relief of infections such as vaginal fungal infections (Sawyer et al., 1975; Christensen and Buch, 1982). This is not unexpected, since Natamycin is virtually insoluble in most solvent vehicles hence, topical formulations of Natamycin consist of mainly crystallized Natamycin suspended in a cream base. The art has also not addressed the concentrations of solubilized Natamycin that is available in these formulations versus the concentration of Natamycin suspended in crystallized form in the ointment base.

Although, there are reports of success with the crystalline suspensions of pimaricin in corneal fungal infections (Lavingia and Dave, 1986) and the prevention of such infections in contact-lens users, the amount of soluble and biologically active pimaricin in these formulations is very small. These opthalmologic studies have however demonstrated the superiority of pimaricin as compared with AMB in regards to local tissue tolerance to polyene antibiotic treatment. Thus, the insolubility of pimaricin is an obstacle that needs to be overcome.

As described in U.S. Pat. No. 6,045,815, the present inventors have had success in solubilizing pimaricin for parenteral formulations. Parenteral formulations of pimaricin are useful in treating systemic infections such as disseminated fungal infections that are often seen in patients with hematological cancers. Such parenterally acceptable, nontoxic formulations of pimaricin are beneficial not only for cancer patients, but also for other groups of immuno-compromised patients, e.g. those suffering from HIV and those having recently undergone open heart surgery, all of which are commonly targets for opportunistic systemic infections.

However, to date there is no topical formulation of pimaricin that has solubilized pimaricin that is in a form that is available to combat infections. Given that a variety of pathogens that are normally susceptible to pimaricin cause topical infections such as but not limited to vaginal infections, ano-genital infections, skin infections, athletes foot, and the like, the development of an effective topical pharmaceutical formulation with activity against a variety of infectious agents is highly desirable.

SUMMARY OF THE INVENTION

The present invention relates to drug formulations that are useful for the treatment, prevention and suppression of infections caused by infectious pathogens such as fungi and microbes. Microbes are exemplified by organisms such as bacteria and viruses. Some exemplary fungal pathogens include those of the *Candida, Trichomonas, Aspergillus* and *Fusarium* species.

The invention provides pharmaceutically acceptable topical antifungal and/or an anitmicrobial compositions that comprise: an amount of pimaricin or a salt thereof that is effective to inhibit the growth of an infectious pathogen in a mammal; a pharmaceutically acceptable dipolar aprotic solvent or an acid; and a pharmaceutically acceptable aqueous secondary solvent.

In some embodiments, the final composition is substantially free of the aprotic solvent and/or the acid. By substantially free it is meant that the composition is about 80 to about 99% free of organic solvents. Therefore the composition may be about 80%, 81%, 82%, 83%, 84%, 85%, 86%, 87%, 88%, 89%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or about 99.9%, free of the aprotic solvent and/or the acid. Intermediate ranges such as 98.75% etc., are also contemplated.

In other embodiments, the final composition is free of the aprotic solvent and/or the acid. By free of the aprotic solvent or acid it is meant that the composition has no detectable levels of dipolar aprotic solvent or solvent.

In some embodiments, the composition further comprises an ointment and/or a cream base. The ointment base can comprises one or more of petrolatum, mineral oil, ceresin, lanolin alcohol, panthenol, glycerin, bisabolol, cocoa butter and the like. The ointment or cream may be any commonly known commercially available ointments or creams such as Aquaphor™ or Eucerin™.

In some embodiments, the acid is a carboxylic acid and is exemplified by acetic acid. In other embodiments, the acid may be hydrochloric acid. The compositions of Natamycin dissolved in acetic acid as a primary solvent provide concentrations ranging from about 3 mg/ml to more than about 500 mg/ml of the active drug which is a broad and effective range for topical administration of doses necessary to yield active antibiotic concentrations that are effective to eradicate localized infections sensitive to this drug.

In other embodiment, the primary solvent is a aprotic solvent such as N,N-dimethylacetamide (DMA) and dimethyl sulfoxide (DMSO), polyethylene glycol (PEG) or polypropylene glycol (PE).

In other embodiments, the aqueous secondary solvent is a surfactant. Surfactants are well known in the art and are organic lipid compounds that are normally produced by the lung tissue and help with the opening of the alveolar constrictions during breathing. Surfactants are also commercially available.

In still other embodiments, the aqueous secondary solvent is an aqueous lipid emulsion. The aqueous lipid emulsion can comprise a lipid component that includes at least one vegetable oil and at least one fatty acid. Such a lipid component can comprise at least about 5% by weight soybean oil and at least about 50% by weight fatty acids. In some embodiments, the lipids in the composition are preferably present in a form other than liposomes, for example, at least about 50% by weight of the lipid is not in the form of liposomes, more preferably at least about 75%, and most preferably at least about 95%.

In other embodiments the secondary solvent can be water, a saline solution, or a dextrose solution.

The invention also provides methods of preventing or treating a localized infection in a mammal, comprising administering to a mammal any of the pharmaceutically acceptable compositions described above.

The method administering can be topical by application of an ointment to the locally infected area or may be by inhalation or nebulization of the respiratory pathways in the case of respiratory tract infections. The composition may be administered by aerosolization to an affected mucosal membrane.

One of skill in the art will recognize that any local infection that is caused by a pathogen sensitive to Natamycin may be treated by the methods of the invention. Non-limiting examples of such infections are vaginal infections, perirectal infections, skin infections, infections of the ingunal area, mucosal infections, intertriginous infections, scalp infections, infections of the outer ear canal, or respiratory tract infections.

Compositions of the present invention can further include additional pharmaceutically acceptable carriers, adjuvants, and/or biologically active substances. Compositions of the present invention, as described above, can be used in methods for treatment or prophylaxis of infections in mammals, particularly in humans. The methods involve administering to a mammal an amount of the compositions effective to prevent, eliminate, or control the infection. The administering step can suitably be topically. The compositions can also be administered intranasally as an aerosol. Such administration is preferably repeated on a timed schedule, and may be used in conjunction with other forms of therapy or prophylaxis, including methods involving administration of different biologically active agents to the subject. The dose administered of a composition in accordance with the present invention is preferably between approximately 1 mg/ml and 500 mg/ml. Thus, it is contemplated that doses of 1 mg/ml, 2 mg/ml, 5 mg/ml, 10 mg/ml, 15 mg/ml, 20 mg/ml, 25 mg/ml, 30 mg/ml, 35 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, and 500 mg/ml are contemplated. One of skill in the art will recognize that this also includes intermediate ranges such as 1.5 mg/ml, 11.1 mg/ml, 115 mg/ml and the like. Of course, the exact dosage to be used will be determined based on the age and disease status of an individual patient by a skilled physician.

The invention also provides antifungal and/or an antimicrobial composition pharmaceutically acceptable for local administration, comprising: an amount of pimaricin or a salt thereof effective to inhibit the growth of a pathogen in a mammal; acetic acid; and an aqueous secondary solvent.

In some embodiments, the acetic acid may be further removed to obtain compositions that are either substantially free or completely free of acetic acid. Some examples of methods for removing acetic acid include lyophilization and/or neutralization using a base. However, it is contemplated that any other method known in the art to remove acetic acid may be used.

In one embodiment, the aqueous secondary solvent may be a surfactant. In another embodiment, the aqueous secondary solvent a lipid emulsion that comprises at least one vegetable oil and at least one fatty acid. The composition can further comprises an ointment and/or a cream base.

The invention also provides methods of preventing or treating a local infection in a mammal, comprising the step of administering topically to a mammal a composition as described above.

The invention also provides pharmaceutically acceptable antifungal and/or antimicrobial compositions that are substantially free of aprotic solvents or acids prepared by the method comprising: obtaining pimaricin or a salt thereof; dissolving the pimaricin in a pharmaceutically acceptable dipolar aprotic solvent or an acid; further dissolving the composition in a pharmaceutically acceptable aqueous secondary solvent; and removing the dipolar aprotic solvent or the acid from the composition.

In some embodiments, the composition is made by a method that further comprises adding to the composition an ointment and/or a cream base.

In some embodiments, the acid is acetic acid. In other embodiments, the acid is hydrochloric acid. In yet other embodiments, the aprotic solvent is selected from the group comprising DMSO, DMA, PE, or PEG.

In some embodiments, the aqueous secondary solvent is a surfactant. Surfactants are well known in the art and are organic lipid compounds that are normally produced by the lung tissue and help with the opening of the alveolar constrictions during breathing. Surfactants are also commercially available.

In still other embodiments, the aqueous secondary solvent is an aqueous lipid emulsion. The aqueous lipid emulsion can comprises a lipid component that includes at least one vegetable oil and at least one fatty acid. Such a lipid component can comprise at least about 5% by weight soybean oil and at least about 50% by weight fatty acids.

In other embodiments the secondary solvent can be water, a saline solution, or a dextrose solution.

Although the present invention is especially useful for preventing or treating systemic fungal infections, it can also be used for prevention and treatment of systemic infections caused by other infectious agents that are sensitive to pimaricin in vivo, such as viruses.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
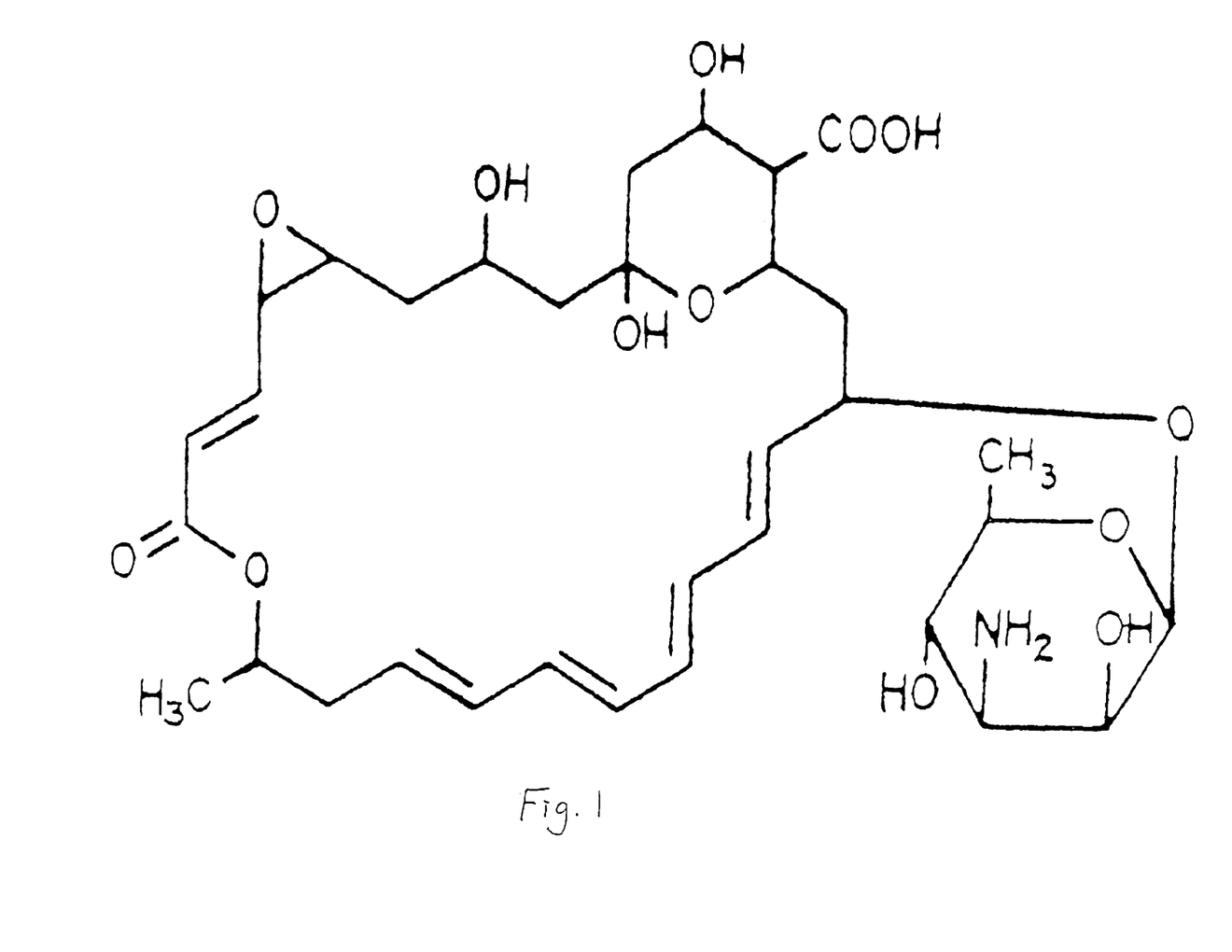
FIG. 1: Chemical structure of pimaricin as free drug.

The following abbreviations are used in this patent:
AMB: Amphotericin B.
Aquaphor™: Comprises Petrolatum, Mineral Oil, Ceresin, Lanolin Alcohol, Panthenol, Glycerin, Bisabolol.
ATCC: American Tissue Culture Collection, Rockville, Md.
DMA: Anhydrous N,N,-dimethylacetamide.
DMF: Dimethylformamide.
DMSO: Dimethylsulfoxide.
FDA: U.S. Food and Drug Administration.
HAc: Glacial acetic acid.
HCl: Hydrochloric acid.
HPLC: High pressure liquid chromatography.
HL-60: Human mycloid leukemia cell line.
IMDM: Iscove's modified Dulbecco Medium (GIBCO, Grand Island, New York, N.Y.).
Intralipid™: Brand name of an aqueous lipid emulsion, made from soy bean oil, and marketed for parenteral nutrition by Clintec.
KBM-7/B5: Human myeloid leukemia cell line.
MeOH: Methanol.
MIC: minimum inhibitory concentration.
MTT: 3,[4,5-dimethylthiazol-2-yl]2,5-diphenyltetrazolium-bromide.
NCI: National Cancer Institute.
NS: Normal saline (150 mM NaCl).
PEG: Polyethylene glycol-400.
PG: Polypropylene glycol/1,2-propylene diol.
RT: Room temperature (22° C.)
SDS: Sodium dodecyl sulphate.
The Present Invention Pimaricin or Natamycin is a drug with a wide-spectrum of antibiotic effects. However, its insolubility makes it largely unavailable for medical utility. In U.S. Pat. No. 6,045,815, the inventors have described solubilized compositions of Pimaricin which are suitable for parenteral use, methods for solubilization of Pimaricin and methods for using solubilized Pimaricin to treat systemic infections.

In the present invention, the inventors have developed pimaricin compositions suitable for topical use where pimaricin or a salt thereof is dissolved using a dipolar aprotic solvent or an acid as the primary vehicle and then further dissolved in one or more secondary cosolvent(s) to increase the drug's aqueous solubility and stablity. In some embodiments, this composition can be combined with ointments or cream bases to allow topical applicability. Alternatively, the composition can be in the form of an aerosol or a spray for other forms of topical administration. In other embodiments, the dipolar aprotic solvent and/or acid, which are often agents that are not pharmaceutically acceptable in large doses, can be removed completely or substantially to pharmaceutically acceptable levels.

Employing a variety of assays the inventors have demonstrated that the resulting Pimaricin formulations are stable for many weeks at room temperature, and that they retain full antifungal activity when applied topically to immunocompromized, infected animals. As described later animal models of topical infection can be used to demonstrate the efficacy of the formulations of the invention. The topical Natamycin formulations of the invention permit what has heretofore been impossible, safe topical administration of fully solubilized drug that is highly effective against pathogens and has negligible toxicity and yields negligible Natamycin plasma concentrations.

The present invention therefore, provides a solubilized topical Natamycin formulation that makes available high concentrations of the active drug. The formulation of the invention may be further mixed in an ointment or cream base. This composition is also highly shelf-stable. Thus, the invention provides a formulation of Natamycin that can be used effectively against a wide variety of pathogens, including, azole resistant yeast species, as well as a variety of molds that cause infections such as, localized *Aspergillus, Fusarium,* and mucor infections that are inherently resistant to commonly available alternative treatments, i.e., azoles and AMB.

Thus, the invention provides methods for the treatment of a wide variety of pathogens including microbes and fungi. Some examples of fungal pathogens that are susceptible to Natamycin include molds and yeasts. Specially localized skin and mucosal infections may be treated and/or prevented by the methods of the invention. In addition, to topical treatments for the localized infections with the formulation of the invention, the inventors also contemplate that the formulation may be administered by aerosolization or nebulization so that the composition may be inhaled to treat respiratory track infections.

As solubilized Natamycin has antibiotic activity against *Fusarium* species as well as *Aspergillosis* sepcies use of the formulation will significantly improve the existing therapeutic armamentarium against opportunistic fungal pathogens that first infect the skin or mucosal surfaces and eventually gain entry into an organism causing wide-spread systemic infections.

Additionally, Natamycin is known to have low local organ toxicity, broad antifungal spectrum activity, predictable lack of systemic absorption after topical administration and activity against numerous pathogens. Natamycin is recognized by the FDA as a GRAS compound (Generally Regarded As Safe). Therefore, the invention provides formulation of Natamycin that are physiologically compatible with topical application in man and domestic animals.

Also provided is a high-pressure chromatography technique that allows the accurate determination of low concentrations of Natamycin in various solvent systems and in biological fluids, i.e., blood plasma.

Solubilization of Natamycin

The present invention involves methodology for solubilization of Natamycin in pharmaceutically acceptable, chemically diverse vehicles, such that the drug remains chemically stable and can be administered topically without undue toxicity from undissolved drug and/or from the solvents at drug doses predicted necessary to obtain clinically significant antibiotic effects.

The present invention involves solubilization of pimaricin in pharmaceutically acceptable vehicles, such that the drug remains chemically stable and can be further formulated into an ointment or cream and administered topically without undue toxicity from the solvents at drug doses necessary to obtain clinically significant antibiotic effects.

Pimaricin is available from Gist-Brocades N.V. (Netherlands) and Sigma Chemical Co. (Saint Louis, Mo.). Pimaricin optionally can be used in compositions of the present invention in the form of one of its antifungal derivatives, such as a salt of pimaricin (e.g., an alkali salt or an alkaline earth salt).

The present inventors have formulated topical formulations of pimaricin which are lipid based, i.e., in the form of creams, ointments, gels, which are suitable for topical treatments. The inventors have successfully used acetic acid as a primary solvent to dissolve the pimaricin. Other primary solvents are DMSO, glycerol, 1,2,-propylene-diol, (PG), and polyethylene glycol-400 (PEG). The Natamycin formulation is further miscible in secondary solvents, examples of which are normal saline, dextrose in water (5% or 10%), and an aqueous soy bean lipid emulsion (Intralipid™). These solvents are examples of vehicles in which pimaricin can be suitably solubilized, yet be safe for human administration, alone or in combinations with other drugs. The solubility of pimaricin in individual solvent vehicles is shown in Table 1 below.

TABLE 1

Solvents Tested for Solubilization of Pimaricin

| Formulation | Time Allowed to Solubilize (hr) | Maximum Solubility (mg/ml) | Vehicle |
| --- | --- | --- | --- |
| 1 | 4 | 2 | DMSO |
| 2 | 4 | 10 | DMA |
| 3 | 6 | 100 | DMA |
| 4 | 4 | 0.078 | PG |
| 5 | <0.2 | >300 | HAc |
| 6 | 4 | N/S | Castor oil |
| 7 | 4 | N/S | PEG400 |
| 8 | 4 | N/S | Intralipid |

(N/S indicates that pimaricin was not soluble in that solvent.)

The described vehicles can be utilized to dissolve Natamycin in concentrations ranging from about 1 mg/ml to more than about 100 mg/ml. For example, an enhanced solubility of >300 mg/ml was achieved by lowering the pH drastically by dissolving the drug in glacial acetic acid, and thereafter mixing it with a secondary solvent, such as a soybean lipid emulsion exemplified by Intralipid™.

This range should cover the administration of doses necessary to yield active antibiotic concentrations in vivo to eradicate superficial infections sensitive to this drug. The invention will therefore allow the introduction of Natamycin in clinical practice for the therapy of localized infections such as vaginal and/or dermatological infections.

In a broader sense, the present invention provides a method to administer Natamycin topically to achieve very high local concentrations without achieving any systemic concentration of the drug. The topical application approach will provide an opportunity to investigate the outstanding therapeutic potential of this agent. These have previously been hampered by the drug's perceived lack of solubility in clinically acceptable solvents for both systemic and topical administration.

The objective of this invention includes the topical administration of Natamycin to improve the control of localized infections that are sensitive to this agent. Infections by various *Candida* species are a paradigm for such infections. Topical use of a fully solubilized Natamycin formulation has not been previously investigated in the practice of medicine, although the drug has well documented anti-fungal properties in vitro, and some antifungal activity has been reported in crystalline suspensions of the drug (Struyk et al., 1957–1958; Korteweg et al., 1963; Raab, 1972).

Virtually no Natamycin is absorbed through the intestinal tract after oral administration, making it impossible to even investigate its use as an orally administered antibiotic against infections. Topical administration would be the logical approach to evaluate Natamycin as therapy for local, antibiotic resistant but potentially serious infections. Unfortunately, the drug has an exceedingly low solubility in most physiologically acceptable solvents that would be compatible with further dilution in an acceptable ointment for routine clinical use in man and domestic animals (Raab, 1972).

Based on the principle of cosolvency (Spiegel and Noseworthy, 1963; Yalkowsky and Roseman, 1981), the composite diluent vehicles rapidly solubilize Natamycin without destroying its antifungal properties. Further, the preferred vehicles are nontoxic and safe for administration in large as well as small animals, and should be acceptable for human administration in the proposed concentrations and total doses to be utilized; indeed, HAc, DMSO, and PG have previously been used for solubilization of various pharmacologically active agents used in man (U.S. Dept. of Health and Human Services, 1984; Weiss et al., 1962; Kim, 1988). DMSO is also extensively used as a cryoprotective agent for low-temperature storage of human bone marrow and peripheral blood derived hematopoietic stem cell preparations to be used for transplantation after high-dose chemotherapy (McGann, 1978; Gorin, 1986; Davis and Rowley, 1990; Gorin, 1992). No serious adverse effects have been experienced from the use of these agents. The clinical use of normal saline, dextrose in water (70%), and aqueous lipid emulsions as well as various ointments are well established means to alter dermal elasticity, promote wound healing and to combat infections.

Data obtained in the rodent model demonstrates that the Natamycin formulations allows reproducible topical treatment of localized infections and provides superior infection control without systemic side effects. Upon topical application the plasma concentrations of Natamycin clearly remained in the undetectable range whereas the antifungal activity remained at its peak for prolonged time periods. The fungicidal range was established by in vitro studies of antifungal activity against *Candida* species, *Aspergillus* species, and *Fusarium* species. Specifically, the novel Natamycin/HAc/lipid solution is chemically stable and simple to handle at room temperature (RT) and can be further mixed with an ointment base such as Aquafor™.

The formulations of the invention provide reliable and easily controlled dosing with a retained and highly effective antifungal effect. The addition of a lyophilization step substantially eliminates the DMA, HAc, or other dipolar aprotic solvent or acids, from the final clinical "working solution", thereby abolish the potential for adverse reactions related to the drastically lowered pH attained with the use of HAc as the primary solvent. This added step should therefore assist in maximizing patient safety after drug administration.

In the case of vaginal infections that can be treated by the methods of the invention, if the composition is made using Hac, it may be of some advantage to retain some of the HAc in the Natamycin formulations such that the lower pH corresponds to the vaginal pH. Thus, the skilled artisan can decide how much, if any, of the acid or dipolar aprotic solvent is acceptable in a final composition.

The design of a pharmaceutically acceptable and safe formulations of Natamycin allows the investigation of its clinical usefulness against localized infections. One can use mycoses as a paradigm of localized infection in immunocompromised patients. In cancer patients, the access to topical Natamycin might be particularly important, since their possible assimilation of infectious agents through impaired mucosal surfaces might predispose them for secondary systemic fungal infections. Further, the availability of Natamycin for effective and reliable topical administration will for the first time make it possible to clinically compare the activity of Natamycin against that of "the gold standard Monistat™", for the treatment of vaginal yeast infections.

In summary, certain infections in diabetic and/or immunocompromised patients, e.g., those caused by various yeast species or molds, particularly *Fusarium*, may be eradicated by Natamycin. In fact, Natamycin may be the only effective drug for the treatment of azole resistant yeasts, which are becoming gradually more widespread with the rapidly increasing indiscriminant use of azoletherpay (primarily fluconazole). The design of a nontoxic, pharmaceutically acceptable, water miscible, topical formulation of Natamycin eliminates the risk of treatment failure from the suboptimal bioavailability of incompletely solublized drug. The addition of a lyophilization step in the preparative procedure will create a Natamycin solvate with minimal acid content. This will reduce the risk of adverse effects related to the vehicle's acid component.

Pharmaceuticals

The pharmaceutical compositions Natamycin for clinical applications will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with formulations of the present invention, its use in therapeutic compositions is contemplated. Supplementary active ingredients also can be incorporated into the compositions.

Administration of these compositions according to the present invention will be via any common topical route so long as the target tissue is available via that route. This includes direct topical administration to an affect area of the skin or mucosal surface or scalp or genital area as well as by inhalation, and nasal, buccal, rectal, vaginal or anal application.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Topical Formulations

To design formulations of Natamycin that are acceptable for topical administration the necessary solubility/stability required is calculated and the formulations are prepared using high pressure liquid chromatographic (HPLC) techniques.

More specifically, one may (1) define the desired solubility and stability of Natamycin in various solvents relevant for topical administration and (2) enhance Natamycin's stable solubility in vehicles acceptable for topical administration, using the rational principle of cosolvency.

Calculation of the Desired Solubility. The inventors have calculated a relevant solubility range for Natamycin by extrapolation from the data obtained from in vitro susceptibility studies of various fungi, such as different strains of Candida and molds. The in vitro antifungal activity of Natamycin solubilized in a few selected solvent vehicles was evaluated using AMB as a reference solution.

Methodology. The antifungal activity of Natamycin was compared with that of amphotericin B utilizing a previously described assay (Anaissie et al., 1991). Briefly, serial dilutions of Natamycin and AMB were mixed in RPMI growth medium with L-glutamine and MOPS-buffer, pH 7.0 (Sigma Chemical Co., St. Louis, Mo.). The different strains of Candida, Aspergillus and Fusarium spp. were then added to the dishes. After incubation at 35° C. for 48 to 72 hours the plates were evaluated for fungal proliferation. The used fungal strains were obtained from the ATCC or isolated from patients, primarily at the MD Anderson Cancer Center. The Natamycin concentrations in the used solutions were assayed with HPLC to assure the highest possible reproducibility of the drug concentrations.

Results

The sensitivity data are displayed in Tables II and III; the activity of Natamycin was similar to that of AMB. Most of the Aspergillus and Fusarium spp. were sensitive to Natamycin, independent of the solvent system. The HAc/Intralipid™ formulation that was lyophilized and reconstituted with distilled water, retained full and stable anti-fungal efficacy, when assayed both after 3 days and after having been stored for more than 2 months at 4° C. All the Aspergillus strains, except for A. flavus, had Natamycin MIC values in the 2–4 $\mu$g/ml (2.1–4.2 M) range. The tested A. flavus was also sensitive to the drug, but with a slightly higher MIC value of 16 $\mu$g/ml (17 $\mu$M). All the tested strains of Fusarium and Candida spp. were sensitive to Natamycin in the range of 2–4 $\mu$g/ml (Tables II and III).

TABLE II

Sensitivity of Fungal Organisms Against Various Pimaricin Formulations

| Organism | Code | L/D $\mu$g/ml | Rm-temp $\mu$g/ml | F/D (nata + lipid) $\mu$g/ml |
|---|---|---|---|---|
| Aspergillus fumigatus | 6-2535 | 2 | 2 | 2 |
| Aspergillus fumigatus | 6-7784 | 2 | 2 | 2 |
| Aspergillus niger | 6-2165 | 2 | 2 | 2 |
| Aspergillus fumigatus | 6-5337-1 | 2 | 2 | 2 |
| Fusarium moniliformi | M6306 | 2 | 2 | 2 |
| Aspergillus flavus | 6-4594-2 | >16 | >16 | >16 |
| Fusarium solanii | s-1184 | 2 | 2 | 2 |
| Candida albicans | ATCC 64545 | 2 | 2 | 2 |

TABLE III

Sensitivity of Fungal Organisms Against Various Pimaricin Formulations

| Organism | Code | Lipid + DMA (1:10) $\mu$g/ml | Nata-lipid 1 $\mu$g/ml | Nata-lipid 2 $\mu$g/ml | AMP + DMSO $\mu$g/ml |
|---|---|---|---|---|---|
| Aspergillus fumigatus | 6-2535 | >16 | 2 | 2 | 0.125 |
| Aspergillus fumigatus | 6-7784 | >16 | 2 | 2 | 0.25 |
| Aspergillus niger | 6-2165 | >16 | 2 | 2 | 0.03 |
| Aspergillus fumigatus | 6-5337-1 | >16 | 4 | 4 | 0.5 |
| Aspergillus flavus | 6-4594-2 | >16 | >16 | >16 | 1 |
| Aspergillus fumigatus | 6-209 | >16 | 2 | 2 | 0.25 |
| Aspergillus fumigatus | 6-0960 | >16 | 2 | 2 | 0.25 |
| Aspergillus fumigatus | 6-1886 | >16 | 4 | 4 | 0.25 |
| Aspergillus fumigatus | 6-1261 | >16 | 4 | 4 | 0.25 |
| Aspergillus flavus | 4-9044 | >16 | >16 | >16 | 1 |
| Aspergillus flavus | 6-5337-2 | >16 | >16 | >16 | 1 |

In Table III, "Lipid+DMA" refers to freshly mixed DMA and Intralipid (1:10, v/v), which exerts no antifungal activity by itself. For "Nata-lipid 1" and "Nata-lipid 2," pimaricin was dissolved in DMA to 100 mg/ml then diluted with 20% Intralipid to 10 mg/ml "use-formulation." "Nata-lipid 1" refers to a formulation where pimaricin was dissolved as above, and after dilution to 10 mg/ml using Intralipid, it was lyophilized. The lyophilized material was refrigerated for 4 months, then reconstituted in normal saline to 10 mg/ml and tested for antifungal activity. "Nata-lipid 2" refers to a formulation where the pimaricin/DMA/Intralipid formulation was prepared as for Nata-lipid 1 and lyophilized immediately, and was reconstituted and tested for antifungal activity three days later. "AMP+DMSO" refers to a formulation of Amphotericin B dissolved immediately prior to use in DMSO, to serve as a positive control.

TABLE IV

Osmotic Pressures of Various Vehicles with and without Pimaricin

| Solution | n | Osmotic pressure MOsm/kg |
|---|---|---|
| Water | 3 | 3 |
| Normal saline | 3 | 233 |
| 5% dextrose in water | 3 | 286 |
| Blood, human | 6 | 280–295 |
| DMA:PEG:PG | 3 | 4492 |
| Pimaricin in DMA:PEG:PG | 3 | 4732 |
| Intralipid | 3 | 340 |
| DMA:Intralipid (1:10, v/v) | 3 | 2067 |
| Pimaricin in DMA:Intralipid (1:10, v/v, fresh) | 3 | 1930 |
| DMA:Intralipid (1:10, lyophil.-reconstit.) | 3 | 157 |
| Pimaricin (1 mg/ml) in DMA:Intralipid (1:10, lyophil.-reconstit.) | 3 | 208 |
| Pimaricin (25 mg/ml) in DMA:Intralipid (1:10, lyophil.-reconstit.) | 3 | 243 |

("n" represents the number of independent determinations.)

Example 2

Preparation of Ointments, Gels, or Creams

Natamycin solubility was determined in several individual vehicles (see Table I). Briefly, a known amount of the drug, as a powder (different lots of purified drug were obtained from Gist-Brocades N.V., Netherlands, and from Sigma Chemical Company, St Louis, Mo.), was equilibrated in the respective solvent at RT (22° C.) over 5 min to 4 hours. An aliquot was then removed and diluted in MeOH prior to HPLC at predetermined times. Based on the Natamycin solubility in these particular vehicles, the inventors attempted to enhance the solubility by mixing different solvents according to the principle of cosolvency (Spiegel and Noseworthy, 1963; Yalkowsky and Roseman, 1981). Several different solvent systems were evaluated relative to the above estimates of necessary solubility to arrive at a clinically relevant optimal stock formulation. This stock formula is then diluted with a "final solvent" to yield the complete working formulation with a Natamycin concentration that can be applied topically without side effects such as inflammation or local irritation. The "final solvent" is preferably one of the commonly available ointment bases, such as petroleum jelly, cocoa butter, Aquaphor™, all of which are readily available and commonly used for topical administration, either for moisturizing purpose or for dissolving various chemically active compounds.

Natamycin Solubility. Several strategies were evaluated to solubilize Natamycin in water-miscible physiologically acceptable vehicles that would be compatible with human topical administration, both on skin and for vaginal administration. The examined solvents included DMA, DMSO, PEG, and PG, and HAc, NS, 5% dextrose in water and further with an aqueous soy bean emulsion (Intralipid™) as secondary solvent. Of these, HAc and DMA were the best primary solvents, providing a solubility in excess of 10 mg/ml. Among these, there is a major difference in solubility between DMA and HAc, in that maximum solubility of >300 mg/ml was reached in HAc within a few minutes whereas maximum solubility in DMA was reached after several hours at RT. However, although Natamycin could be dissolved in HAc and DMA to at least 100 mg/ml, it started degrading already within a few hours in solution. The problem of stabilizing Natamycin once dissolved in HAc or DMA was addressed with the following approach based on the cosolvency principle. First the dissolved Natamycin was stabilized by the addition of an aqueous soy bean lipid emulsion (Intralipid), and the HAc was then removed by lyophilization or through neutralization of the acid by addition of a base in equal amount to a pH in the low-normal range (pH 5.0–6.0). The lyophilized/neutralized Natamycin/lipid formulation was then mixed at high (>30° C.) temperature with the suitable ointment base, such that a composition suitable for topical administration was obtained. In one example, a natamycin ointment was made with HAc as the primary solvent, Intralipid™ as a secondary solvent, followed by mixing in an ointment base exemplified by Aquaphor.

Example 3

Sensitive Detection System

An accurate and sensitive detection system for detecting low concentrations of Natamycin in solution in protein-free mixtures has also been developed by the present inventors. This is an HPLC assay that utilizes absorbance detection with a variable wave length detector operating in the u.v. spectrum at 293 nm, a value chosen on the basis of the inherent absorption maxima of the Natamycin molecule (Raab, 1972).

A liquid chromatographic system equipped with an LDC 4000 multi-solvent delivery system™ and a Waters™ system 717plus Autoinjector™ was used to detect low concentrations of Natamycin. The absorbance detector was a LDC 3100 variable wave length detector in sequence with an LDC model CI 4100 fully computerized integrator. The column used was a Whatman EQC 10 $\mu$l 125A™ C18 column (4.6 mm i.d.×21.6 cm) (Whatman Inc. Clifton, N.J.). The mobile phase system was an isocratic mixture of MeOH (47% v/v), tetrahydrofuran (2% v/v), and $NH_4$-acetate (0.1% w/v) made up to 100% with double-distilled water. All chemicals were HPLC grade unless otherwise indicated. The flow rate was 1.5 ml/min and the recorder's chart speed was 5 mm/min.

HPLC Assay. Two examples of authentic Natamycin chromatograms from the HPLC assay were obtained. The drug was (a) analyzed in the aqueous DMA-Intralipid solvent, and (b) was extracted from human plasma that had been spiked with 5 $\mu$g/ml of natamycin prior to extraction as described above. The retention time under the above conditions was 9.8–10.8 min, and the assay was linear from 100 ng/ml to 25 ng/ml in protein-free solutions, i.e. the various solvent systems utilized in the formulation-feasibility and formulation-stability studies, and from about 50 ng/ml to 1 mg/ml for protein-containing solutions (plasma samples). This assay consistently yielded high recovery, accuracy and a lower sensitivity limit of about 10 ng/ml. The technique was standardized and used without modifications for the studies of both stability and pharmacokinetics.

Example 4

Solubility and Stability Studies of Various Formulations

The objective of the present example was to; (1) design stable Natamycin formulations that are suitable for topical administration; (2) establish the chemical and physical stability of Natamycin in the novel vehicles; (3) establish the solubility of Natamycin in these vehicles when mixed with Intralipid™; and (4) investigate the in vitro properties of these formulations; i.e. parameters such as their osmolarity, hemolytic potential, and cytotoxicity, to show that they are non-toxic, non-irritating and therefore appropriate for the intended topical treatment purposes.

Solubility Studies. An excess amount of Natamycin as a solid powder was added to DMA, DMSO, PEG, PG and HAc at RT. Each mixture was placed in a dark environment and checked visually for up to 4 hours for evidence of solubilization. Samples of 1 ml were taken at various time intervals, and filtered through a 0.45 μm PTFE™ membrane filter fitted to a syringe assembly (Whatman Inc.), and after appropriate dilution, the Natamycin concentration was determined by HPLC.

Stability of the various Natamycin formulations. To study the physical and chemical stability of the various parenteral formulations, three sets of studies were performed:

(a) Natamycin was dissolved at a concentration of 100–300 mg/ml in HAc ("stock solution") and incubated at 4° C., at 22° C. and at 40° C. The drug concentration was analyzed by HPLC in samples taken immediately after solubilization and after gradually increasing time intervals of up to 48 hours.

(b) The Natamycin-HAc stock solution was diluted with PEG/water (1:1:1, v:v:v, HAc:PEG:water), or PG/DMSO (1:1:1, v:v:v), or PG/DMSO/PEG (1:1:1:1, v:v:v:v), or aqueous lipid emulsion (1:10 and 1:100, v:v, HAc:Intralipid™), to yield Natamycin concentrations ranging from 1–50 mg/ml.

(c) The HAc-Natamycin mixture was diluted in NS or 5% dextrose to a drug concentration of 1 mg/ml. (d) The HAc-Natamycin mixture was blended with DMSO and Intralipid™, or directly in Intralipid™.

The various formulations were analyzed by HPLC immediately after mixing, then hourly for 8 hours, and then at gradually increasing time intervals up to several weeks, depending on the rate of degradation in the respective solvent system.

The solubility of the drug differed markedly between different solvents (Table I). Only DMA and HAc, which provided the highest solubility could be considered for extended studies as primary solvents, but since the solubility of Natamycin in DMA was dependent on several hours of incubation, the preferred solvent was HAc, which yielded maximum solubility in a matter of minutes at RT, see below.

To lower the HAc concentration in the final stock- and use-formulations without adversely affecting the drug's shelf life, the inventors investigated lyophilization as part of the preparation of a complete Natamycin/HAc/aqueous lipid-solvate vehicle. The lyophilization step can create a composite solvate containing Natamycin and lipid, but only trace amounts of HAc. The reconstitution of this solvate can be achieved by the addition of distilled water or a buffer only, and the low HAc content and/or the neutral pH of the final solvent system yields a low-acceptable hemolytic potential, and therefore also low inflammatory potential, of the final use-formulation.

In Vitro Cytotoxicity of Natamycin. The cytotoxic potential of selected solvent systems with and without Natamycin was determined against the two human myeloid leukemia cell lines HL-60 (Gallagher et al., 1979) and KBM-7/B5 (Andersson et al., 1987; Andersson et al., 1995), to further assure that the vehicle chosen would have little or no local toxicity against normal human mucosa/skin, using a modification of the previously published MTT assay (Hansen et al., 1989; Andersson et al., 1996). Briefly, HL-60 or KBM-7/B5 cells in Iscove's modified Dulbecco medium (IMDM) supplemented with 10% fetal bovine serum were incubated for 60 min at 37° C. with the complete vehicles (a: HAc/Intralipid™, 1:10, v/v, or c: HAc/Intralipid™, 2:6:3, v/v) at increasing concentrations of the vehicle (0.5%, 1.0%, 2.0%, 3.0%, and 10%, v/v) with or without Natamycin. At the end of the 60 min incubation the cells were washed in ice-cold PBS and resuspended in IMDM with 10% fetal bovine serum at 37° C. Twenty-four hours later 25 μl MTT solution (5 mg/ml) (Sigma Chemicals, St. Louis, Mo.) was added to each sample, and following an additional 2 hours of incubation at 37° C., 100 μl extraction buffer was added (extraction buffer: 20% (w/v) SDS dissolved to saturation at 37° C. in a solution of DMF and deionized water (1:1); pH 4.7). After incubation overnight at 37° C., the optical densities were measured at 570 nm using a Titer-Tech™ 96 well multi-scanner™, against extraction buffer as the calibrating blank. The cytotoxicity was determined as the colorimetric difference between the samples exposed to solvent (Natamycin as above and the background reactivity of cells that had been incubated in parallel in PBS alone. All determinations were performed in triplicate (Hansen et al.,; Andersson et al., 1996).

Hemolysis Studies In Vitro. The inventors employed the procedure of Parthasarathy et al., to examine the hemolytic potential of a few selected preparations (Parthasarathy et al., 1994), and the $LD_{50}$ values of the various formulations were constructed as described. Briefly, heparinized blood was mixed with an equal volume of Alsever's solution. This mixture was washed twice in PBS, and a 10% (v/v) erythrocyte/PBS solution was then prepared and mixed with increasing amounts of the complete solvent system with or without the addition of Natamycin. These mixtures were then incubated for 4 hours at 37° C. At the end of the incubation, the cells were pelleted at 10,000×g in an Eppendorff™ centrifuge, and the release of hemoglobin in the supernatant (i.e. hemolysis) was spectrophotometrically determined at 550 nm. Maximum lysis was measured against a reference solution of erythrocytes that had been completely lysed by hypotonic shock. The hemolytic potential of three of the complete formulations was evaluated as described (Parthasarathy et al., 1994), and the data were plotted as the fraction of healthy cells versus the total volume percent. Total volume percent was defined as the volume percent of the vehicle in the mixture after dilution with blood. This was done in an attempt to simulate the dilution of the respective drug formulation in the bloodstream after parenteral administration. Healthy erythrocytes were defined as those capable of retaining their hemoglobin intracellularly after mixture with the various Natamycin formulations (Parthasarathy et al., 1994).

Results

Equilibrium Solubility and Stability in Various Solvent Vehicles. A maximum equilibrium solubility of Natamycin of >100 mg/ml was achieved in HAc already after 5–10 min at RT, and in DMA after several (>4) hours. The drug formulations in, DMSO, PEG-400 and PG achieved considerably lower equilibrium concentrations (Table I). The latter solvents neither provided an acceptable solubility nor chemical stability of the dissolved drug, and these vehicles were therefore not considered for further studies. Once a Natamycin solubility of 100 mg/ml was reached in anhydrous DMA and HAc respectively, the drug started degrading with a loss of approximately 5–10% over the subsequent 3–4 hours. The drug was more stable when PEG was used as a secondary solvent, but again drug degradation began within another few hours at RT. At 4° C. the drug was more stable, but degradation was still apparent within 8 to 12 hours.

The temperature-dependent stability of solubilized Natamycin in the different solvent systems was studied as follows: The drug was dissolved in HAc at 100 mg/ml, and different aliquots were stored at 4° C., at 22° C., and at 40° C. Immediately after solubilization and at various intervals up to 48 hours later, aliquots from the different samples were analyzed by HPLC. The drug samples stored at 4° C. and at 22° C. degraded slower than those stored at higher temperatures: at 40° C. the Natamycin started degrading within 1 hour after the start of incubation, and at RT there was a loss of 5–10% in the first 4 hours.

When the 20% aqueous lipid emulsion (Intralipid™) was used as a secondary solvent, a different stability pattern was recorded; when the Natamycin concentration was adjusted to 10–50 mg/ml by dilution with 20% Intralipid of the HAc-Natamycin stock solutions, the drug was stable for more than 6 weeks.

As HAc and water have similar boiling points, (116° C. and 100° C., respectively) it was envisioned that the HAc could be effectively removed by lyophilization of the Natamycin/HAc/aqueous lipid complex to create a solvate that was stable yet easily reconstituted by adding only double-distilled water under gentle agitation without any appreciable loss of anti-fungal efficacy, and this assumption proved correct. Indeed, within a few minutes after addition of distilled water to the solvate, the drug was reconstituted at 10–50 mg/ml, without remaining amounts of HAc. This reconstituted Natamycin formulation retained an anti-fungal efficacy that was equivalent to that of the freshly prepared HAc/aqueous lipid formulation when assayed in vitro (see below). This reconstituted formulation was also stable at RT for more than 4 weeks when mixed with an ointment base, Aquaphor. The lyophilized Natamycin formulation remained stable (by HPLC) for more than four months at 4° C. This preparation could still be readily reconstituted to 10 mg/ml within a few minutes with distilled water, with retention of full anti-fungal activity in vitro (see Table II). The inventors further simulated a final clinical use-formulation with a Natamycin of 5 mg/ml by diluting the 50 mg/ml-HAc formulations (prepared fresh with HAc/Intralipid or after lyophilization/reconstitution respectively) with different ointment bases. The "use-formulations" are stabile at RT. Similarly, when HAc and DMSO were used as the primary solvent system prior to mixing with Intralipid and followed by lyophilization, the majority of the organic solvent, here DMSO, was removed and the result was a stable lipid-based solvate was obtained, that could be easily reconstituted to 10 mg/ml under gentle agitation after the addition of distilled water. This reconstituted formulation was also stable for more than 24 hours at RT assessed by HPLC.

Osmotic Pressure. It is desirable that a parenteral formulation of a pharmacologically active agent be isosmotic to blood in order not to cause secondary irritation/inflammation on an already irritated (from infection) mucosal surface or skin. A hypertonic delivery system should therefore be avoided if at all possible. The osmotic pressure of a few of the tested formulations are shown in Table III. A DMA-based formulation with or without Natamycin was very hypertonic and therfore omitted from further testing. In contrast, the HAc/Intralipid preparation was closer to isosmotic, both when prepared fresh and when reconstituted after lyophilization (Table III). Similarly, the lyophilized/reconstituted HAc/DMSO/Intralipid™ vehicle was also close to isosmotic. Adding Natamycin to the respective vehicles did not appreciably change their osmolarity ($P>0.05$).

In Vitro Cytotoxicity of Natamycin. The HL-60 and KBM-7/B5 myeloid cells were exposed to the selected vehicles at increasing volume ratios with or without the addition of increasing drug concentrations. The cytotoxicity of each formulation was then assayed in the MTT assay (Hansen et al., 1989; Andersson et al., 1996). None of the examined solvent systems exerted any detectable toxicity against the cells in this assay.

Hemolysis. The formulations studied showed similar trends for hemolysis with the addition of Natamycin. The Natamycin dependent lysis was noteworthy only at concentrations exceeding 50 µg/ml for the freshly prepared HAc/Intralipid formulation and at 60 µg/ml for the lyophilized-reconstituted HAc/aqueous lipid formulation. The drug-specific hemolysis was highly reproducible between different experiments, as was the internal ranking between the various solvent systems between the different experiments. The detailed data and the individual $LD_{50}$ values of the different vehicles with and without Natamycin were analyzed. In the figures, the $LD_{50}$ was defined as the total volume percent of the drug-vehicle mixture needed to produce 50% hemolysis. The HAc/Intralipid™ "fresh" formulation had a significantly lower hemolytic potential than any of the solvent systems containing organic solvent. Further, the hemolytic potential of the lyophilized HAc/Intralipid formulation was significantly lower than that of the freshly prepared HAc/aqueous lipid formulation for all tested Natamycin concentrations.

Example 5

Quantitative Analysis of Topical Formulations of Natamycin

The inventors have shown that the drug can be recovered from the "final" topical use-formulation exemplified by HAc-Intralipid-Natamycin mixed in a suitable ointment base, intended for application to experimental animals or humans using a quantitative extraction technique and HPLC assay.

Quantitative Extraction of Natamycin From the Complete Use-Formulation. In one specific example, Natamycin in a complete use-formulation of HAc-Intralipid was mixed with a suitable ointment base, Aquaphor™ or petroleum jelly, at Natamycin concentrations of 10–50 mg/ml. The Natamycin was then extracted from the ointment using a slight modification of a method described in U.S. Pat. No. 6,045,815, the contents of which are incorporated herein by reference. Briefly, 0.2 ml ointment was mixed with 0.2 N HCl in MeOH (1:1, v/v), and after thorough mixing by a vortex machine, the sample was extracted with three volumes of hexane. The hexane was separated from the Natamycin by evaporation and the drug was reconstituted in 200 µl of MeOH prior to HPLC. Natamycin was spectrophotometrically detected in the HPLC analysis as described above. The Natamycin recovered from the ointment corresponded to a drug concentration of 10 mg/ml was calculated to be 86±5%. The assay was linear in the interval from 50 ng/ml to 1,000 µg/ml (data not shown).

Example 6

Removal of Dipolar Aprotic Solvent or Acid from the Final Formulation

As described earlier lyophilization or neutralization is used in the methods of the invention to prepare natamycin formulations that are free or substantially free of the dipolar aprotic or acid components to arrive at pharmaceutically acceptable formulations. In this example, lyophilized formulations of natamycin were analyzed by gas-chromatography/mass-spectroscopy (GC/MS) to determine how much organic solvent (dipolar aprotic solvent or acid) is remaining in the formulation following lyophilization.

Gas chromatographic studies, such as the GC/MS methods described herein are typically used in the art as assays to detect the presence of residual organic solvents in compositions such as the instant solvent vehicles. These assays are extremely sensitive and are known to detect organic solvents as low as 10–100 ng/mL. For examples, see Mulligan et al., 1995; Camarasu et al., 1998; Li et al., 2002; that describe the use of gas-chromatography-mass spectroscopy as standard methods to detect the presence of residual solvents.

GC/MS was performed on samples of the instant compositions, exemplified by N'N-dimethlyacetamide (DMA) as a dipolar aprotic solvent and Intralipid (an aqueous lipid emulsion) as a secondary aqueous solvent with or without pimaricin. Thus, in some examples only the solvent vehicle, i.e., without drug was analyzed and in other examples solvent vehicle with pimaricin was analyzed. The standard curve for comparison was prepared using DMA and hexane. Other characteristics of the GC/MS are as outlined below:
GC Injector: 200C
Oven temperature: 40C, 2 min; at 5C/min, to 70C.
Column: ZB-1 15m×0.25 mm×0.251 µm capillary column
GC-MS transfer line: 290C
Ion source temperature: 250C
GC-MS Scan range: 30–500 Dolton
The data obtained are set forth in Table V.

The samples numbered 7, 8 and 9 were prepared as described above for samples 1–6 by mixing DMA and Intralipid (1 ml and 5 ml), 2 ml of which was then lyophilized for 36 hours, followed by reconstitution in 2 ml of saline prior to GC/MS analysis.

The samples numbered 10, 11 and 12 were prepared by mixing the dipolar aprotic DMA (1 ml) with the drug pimaricin at a concentration of 10 mg/ml. This was followed by mixing Intralipid (5 ml). 2 ml of this was then lyophilized for 36 hours, followed by reconstitution in 2 ml of saline prior to GC/MS analysis.

The samples numbered as 13, 14, 15 and 16 in Table V were used to plot a standard curve and demonstrate the linearity of the GC/MS technique for detection of DMA. Samples 13–16 were prepared by mixing 200 µl of DMA and 200 µl of hexane by vortexing for 2 minutes. The mixture was centrifuged for 5 minutes at 2500 rpm, 100 µl of the organic phase was obtained and 1.0 µl of this was injected into the GC/MS. Samples 13–15 were further diluted with hexane to obtain different DMA concentrations of 1.0, 2.5, and 5.0% respectively. These samples were then subject to GC/MS to obtain a standard curve that indicates the linearity for detection of DMA by GC/MS.

As can be seen in Table V, samples that were not lyophilized, represented by sample numbers 1–6, have a peak area of about 16422300 to 18576262 (see column 4 of Table V) which is designated as having 100% of DMA. Samples that were subject to lyophilization, represented by sample numbers 7–12, have a peak area of about 0 in three cases out of six cases and peak areas of 298308, 199250 and 183498 in three other cases. This represents 0% of DMA content for sample numbers 7, 11 and 12 and 1.7% DMA for sample number 8, 1.1% DMA for sample number 9, and 1.0% DMA for sample number 10 respectively (see data in

TABLE V

GC/MS Analysis of the Solvent Vehicle

| Sample Number | Sample Name | DMA ($t_R$) min | Peak Area | Inj. Vol. | GC-MS filename | DMA, % |
|---|---|---|---|---|---|---|
| 1 | 1A | 2.27 | 18576262 | 1.0 | DMA 1A 091302__17 | |
| 2 | 1B | 2.27 | 18087068 | 1.0 | DMA 1B 091302__18 | |
| 3 | 2A | 2.27 | 16525558 | 1.0 | DMA 2A 091302__19 | |
| 4 | 2B | 2.28 | 18284694 | 1.0 | DMA 2B 091302__20 | |
| 5 | 3A | 2.27 | 16866754 | 1.0 | DMA 3A 091302__21 | |
| 6 | 3B | 2.27 | 16422300 | 1.0 | DMA 3B 091302__22 | |
| 7 | I$ | — | 0 | 1.0 | DMA I 091302__30 | 0% |
| 8 | II$ | 2.27 | 298308 | 1.0 | DMA II 091302__31 | 1.70% |
| 9 | III$ | 2.29 | 199250 | 1.0 | DMA III 091302__32 | 1.10% |
| 10 | IV with drug# | 2.29 | 183498 | 1.0 | DMA IV 091302__33 | 1.00% |
| 11 | V with drug# | — | 0 | 1.0 | DMA V 091302__34 | 0.00% |
| 12 | VI with drug# | — | 0 | 1.0 | DMA VI 091302__35 | 0.00% |
| 13 | std crv 1.0%* | 2.46 | 184676787 | 1.0 | DMA std 1% 091302__24 | |
| 14 | std crv 2.5%* | 2.68 | 457137954 | 1.0 | DMA std 2.5% 091302__25 | |
| 15 | std crv 5.0%* | 2.91 | 920448678 | 1.0 | DMA std 5% 091302__26 | |
| 16 | std crv 50%* | 2.69 | 12733869573 | 1.0 | DMA std 50% 091302__28 | |

$The sample numbered 7–9 refer to the "solvent vehicle".
In sample numbers 10–12 "drug" refers to the addition of pimaricin to the solvent vehicle.
*The samples for the standard curve (std crv), numbered 13–16, were prepared by mixing DMA and Hexane (1:1) (Li et al., 2002).

The samples numbered 1, 2, 3, 4, 5, and 6 in Table V were prepared by mixing DMA and Intralipid (1 ml and 5 ml), 2 ml of which was analyzed for DMA content by GC/MS prior to lyophilization. These samples are designated as having 100% DMA content.

column 7, Table V). Thus, 3 out of 6 samples had no detectable DMA, indicating that all the DMA was eliminated from these samples while the remaining three samples had 1.7%, 1.1% and 1.0% of DMA indicating that only trace amounts of DMA is retained or that virtually all the DMA is eliminated from these samples. Thus, 98% or more of the organic solvent can be removed from the solvent vehicles by the methods described in the above-referenced patent application.

As described by the analysis of the GC/MS data, the samples of solvent vehicle and drug samples numbered 10, 11 and 12 that were prepared by mixing the dipolar aprotic DMA (1 ml) with the drug pimaricin at a concentration of 10 mg/ml were "free" of the DMA in the cases of samples number 11 and 12 with 0.0% being detected and "substantially free" of DMA in sample 10 with only 1% being detectable. In the examples of "solvent vehicle" alone, the DMA content was "virtually eliminated" in 3 out of six cases (with only 1.7%., 1.1% and 1.0% being detected in these samples) and "eliminated" in the other 3 samples where no detectable DMA was seen. Thus, 98% or more of the dipolar aprotic solvent or acid is eliminated by these methods resulting in final compositioins of natamycin that are free or substantially free of organic solvents.

One of skill in the art will appreciate that in order to make a pharmaceutically acceptable formulation all of the dipolar aprotic solvent or acid can be removed if required by extending lyophilization times. However, removal of all the dipolar aprotic solvent or acid may not be necessary in some cases. For the purpose of making a "pharmaceutically acceptable vehicle" removal of dipolar aprotic solvents or acids to an acceptable amount may be required by a health regulating body. The removal of dipolar aprotic solvent or acid component minimizes the side effects from contaminant organic solvent in the final use pharmaceutical formulations.

Example 7

Animal Models of Infection

The efficacy of the topical formulations of the invention can further be analyzed using animal models of infections. For example, one of skill in the art can contemplate testing the topical formulations of the invention using animal models such as the rodent models. Some examples of rodent models used in the art are described in Black et al., 1999; Ghelardi et al., 1998; Foldvari et al., 2000; Jansen et al., 1991; Larsen and Galask, 1984; the entire contents of which are incorporated here by reference. Described below is a rodent model of vaginal yeast infection which can be used.

Intravaginal Infection Model. An in vivo assay to test the antifungal properties of a topical natamycin preparation, made by the methods of the invention, may be done on a rodent model of vaginal yeast infection. Rodents models are useful due to their high reproducibility, ability to be pharmacologically manipulated to be immunosuppressed, and their vaginal tract can be easily evaluated for the local adverse effects of polyenes and other antifungal agents. After immunosuppression with estrogen derivatives +/–progesterone would be administered subcutaneously prior to vaginal inoculation with yeast. The Natamycin compositions of the invention, exemplified in one instance by HAc/Intralipid™ mixed in an ointment base, e.g. Aquaphor™, would then be administered intravaginally in a small volume (not exceeding 100 µL). To assure reproducibility of the experimental conditions, the experiments would be staggered; one set of animals rats at each of several dose levels would be started on consecutive days, and repeat experiments would be performed after 2 weeks. The investigation would be performed in female rats weighing 150–250 g. Blood samples would be obtained for determination of Natamycin plasma concentrations at 1 and 4 hours after the intravaginal drug application. All animals would be allowed free access to food and water. The Natamycin administration would be repeated on day 3, and again blood samples would be accrued to determine possible drug adsorption from the mucosal surface into the blood stream with this mode of application. The antifungal treatment effect would be evaluated as the fraction of animals clearing the infection versus untreated control animals within a 7-day period. The blood samples would be centrifuged at 1,000×g for 10 min, and the plasma separated and stored at –80° C. until assayed by HPLC.

Natamycin in Plasma. The drug extraction with hexane and MeOH from plasma is essential to avoid interference from endogenous plasma components and to recover the maximum amount of drug. Authentic chromatograms from blank plasma, Natamycin-spiked plasma, and one example of that obtained after extraction of a plasma sample from the proposed study would be expected to demonstrate that there is negligible adsorption of Natamycin to the blood after topical/vaginal application. The Natamycin retention time in this system is 11.1–12.0 min. The recovery of Natamycin with the above described technique is 91±5% when human plasma is spiked in vitro with 10 µg/ml of drug. The assay is linear after drug extraction from plasma samples in the range from 50 ng/ml to 1.0 mg/ml. When a standard curve was prepared in the concentration range from 100 ng/ml to 25 µg/ml, a good correlation has been obtained between the plasma Natamycin concentration and peak AUC value:

$$AUC = 1.2209e+4 + 3.2994e+5x, \; r^2 = 1.00 \qquad (Eq. 1)$$

The in vivo peak plasma Natamycin concentrations after topical administration of the above formulation would be plotted for several dose levels at the end of a 1-hour observation and a 4-hour observation time; there should not be any detectable Natamycin recovered from the animal's blood after such administration.

The in vitro data demonstrates that the successful design of pharmaceutically acceptable topical formulations of Natamycin can be accomplished, ones that are compatible with ointment bases available for topical application, i.e. on the skin, or intravaginally. These formulations should be accepted with good tolerance and negligible toxicity, as could be demonstrated using the intravaginal route in a rodent model. The topical application of one of the preparations in this rodent model should not provide any detectable plasma drug concentrations over a 4-hour observation interval, and should maintain fungicidal Natamycin concentrations without discernible untoward effects on the animals' clinical performance as detected by assessment of their infectious state after a 7-day observation period. It should be noted, that for such experiments the inventors would select a "fresh" HAc/aqueous lipid formulation without organic solvent, considering the potential for an adverse influence of the solvent system on the local vaginal mucosa. Further, by instead of utilizing a topical ointment base one can conceive of using a secondary solvent of the group including surfactant. This would enable application of Natamycin by inhalation to prevent the early infection of the upper airways of animals and man.

The data obtained with several diverse formulations demonstrate conclusively, that it should be feasible to introduce topical fully solubilized Natamycin in clinical therapy of localized fungal infections including those caused by *Candida* spp., *Aspergillus*, and *Fusarium*, with the predictable attainment of antibiotic activity, and with a reasonable expectation of low normal organ toxicity. The inclusion of a lyophilization step in the formulation procedure significantly increased the stability/shelf-life of the final formulations. This step would virtually eliminate the containment of organic solvent from the final use preparation, and the inventors expect it not only to further reduce the risk of solvent system toxicity, but also to minimize the risk that an organic solvent could potentiate clinical adverse effects related to Natamycin.

Novel vehicles have been invented for the stable, pharmaceutically acceptable formulation of Natamycin to make it safe to administer this drug topically as treatment of localized fungal infections The inventors first established a sensitive and specific HPLC assay, which allowed the reproducible quantitation of Natamycin concentrations as low as 10–20 ng/ml. In parallel, the inventors developed extraction techniques to recover Natamycin in a reproducible manner from topical formulations and from blood plasma samples. Thereafter, stability studies of newly formulated parenterally compatible vehicles was initiated to select the best formulations to study the hemolytic potential as a surrogate marker for mucosal irritation/inflammation secondary to topical adminstration of the derived formulations, and the inventors also examined the in vitro fungicidal activity of prototyope formulations, such a novel preparation was clearly fungicidal, based on the in vitro sensitivity studies with Natamycin against several strains of Candida spp., Aspergillus spp. and against Fusarium spp. The in vitro sensitivity studies employed various fungal organisms as a paradigm for infectious organisms that are sensitive to the drug. It is contemplated that the stable and non-toxic novel Natamycin formulations will be useful as topical treatment of fungal infections in an experimental setting or as a prophylactic agent that can be given either topically (on the skin or intravaginally) or through nebulization. Ultimately, clinical studies of Natamycin's efficacy against localized infections are envisioned. The present invention allows one to investigate the beneficial effects of fully solubilized Natamycin against localized infectious agents with the potential for a major improvement in the outcome of such infections.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,045,815
Anaissie et al., Antimicrob. Methods Chemother., 35:1641–1646, 1991.
Anaissie et al., Eur. J. Clin. Microbiol. Infect. Dis., 8:323–330, 1989.
Andersson et al., Cancer Chemother. and Pharmacol., 38:406–416, 1996.
Andersson et al., Cancer Genetics and Cytogenet., 24:335–343, 1987.
Andersson et al., Leukemia, 9:2100–2108, 1995.
Black et al., J. Reproductive Immunology, 45:1–18, 1999
Camarasu et al., Pharm. Biomed. Anal. 18:623–638,1998.
Christensen and Buch, Acta Obstet. Gynecol. Scand., 61(4):325–328, 1982.
Davis and Rowley, Amer. Assoc. Blood Banks, 41–62, 1990.
Foldvari et al., Mycoses, 43(11–12):393–401, 2000
Gallagher et al., Blood, 54:254–68, 1979.
Ghelardi et al., Antimicrobial Agents and Chemotherapy, 42:2434–2436, 1998.
Gorin, Clin. Haematol., 15:19–48, 1986.
Gorin, In: Bone marrow and stem cell processing: A manual of current techniques, Areman et al. (Eds), F. A Davis Company, Philadelphia Pa., 292–362, 1992.
Hansen et al., J. Immunol. Methods, 119:203–210, 1989.
Jansen et al., Am. J. Obstet. Gynecol., 165:1551–57, 1991
Kim, Drug Metab. Rev., 19:345–368 1988.
Korteweg et al., Antibiot. Chemother., 11:261–72, 1963.
Larsen and Galask, J. Repr. Medicine, 29:863–68, 1984
Lavingia and Dave, Indian J. Ophalmol., 34:73–77, 1986.
Li et al., Pharm. Biomed. Anal., 28, 673–682, 2002.
McGann. Cryobiology, 15:382–90, 1978.
Mulligan et al., J. Chromatogr. Sci. 33:49–54, 1995.
Natamycin, CAS Reg-No. 7681–93–8, Jun. 22, 1982. Code of Federal Regulations, Food and Drugs, .sctn. 172.155, volume 21, revised Apr. 1, 1995.
Parthasarathy et al., Cancer Chemother. Pharmacol., 34:527–34, 1994.
Raab, In: Natamycin (pimaricin): Its properties and possibilities in medicine, Georg Thieme Publishers, Stuttgart, Germany. 1972.
Remington's Pharmaceutical Sciences, 15th Edition, pages 1035–1038 and 1570–1580, 1980.
Sawyer et al, Drugs, 1975;9(6):406–23.
Spiegel and Noseworthy, J. Pharm. Sci., 52:917–927, 1963.
Struyk et al., Antibiot. Ann., 878–85, 1957–1958.
U.S. Department of Health and Human Services: NCI Investigational drugs. NIH Publication No. 84–2141, 1984.
Weiss et al., Cancer Chemother. Rep., 16:477–485, 1962.
WO 93/07884
Yalkowsky and Roseman, In: Techniques of solubilization of drugs, Yalkowsky (Ed.), 91–134, Marcel Dekker Inc., NY, N.Y., 1981.

What is claimed is:

1. A pharmaceutically composition comprising:
    a) an amount of pimaricin or a salt thereof that is effective to inhibit the growth of an infectious pathogen in a mammal;
    b) a pharmaceutically acceptable dipolar aprotic solvent or acid; and
    a pharmaceutically acceptable aqueous solvent comprising a lipid component.

2. The composition of claim 1, wherein the final composition is substantially free of the aprotic solvent and/or acid.

3. The composition of claim 2, wherein the final composition free of the aprotic solvent and/or acid.

4. The composition of claim 1, wherein the acid is acetic acid.

5. The composition of claim 1, wherein the aprotic solvent is DMA, DMSO, PEG or polypropylene glycol.

6. The composition of claim 1, wherein the aqueous solvent comprises an aqueous lipid emulsion.

7. The composition of claim 6, wherein the aqueous lipid emulsion comprises a at least one vegetable oil and at least one fatty acid.

8. The composition of claim 7, wherein the lipid component comprises at least about 5% by weight soybean oil and at least about 50% by weight fatty acids.

9. The composition of claim 1, wherein the solvent comprises a saline solution.

10. The composition of claim 1, wherein the solvent comprises a dextrose solution.

11. A pharmaceutically acceptable composition prepared by the method comprising:
   a) obtaining pimaricin or a salt thereof;
   b) dissolving the pimaricin in a pharmaceutically acceptable dipolar aprotic solvent or acid;
   c) further dissolving the composition of step b) in a pharmaceutically acceptable aqueous secondary solvent; and
   d) removing dipolar aprotic solvent or the acid to render said composition free or substantially free thereof.

12. The composition of claim 11, wherein the acid is acetic acid.

13. The composition of claim 11, wherein the aprotic solvent is selected from the group comprising DMSO, DMA, polypropylene glycol, or PEG.

14. The composition of claim 11, wherein the aqueous secondary solvent comprises an aqueous lipid emulsion.

15. The composition of claim 14, wherein the aqueous lipid emulsion comprises a lipid component that includes at least one vegetable oil and at least one fatty acid.

16. The composition of claim 15, wherein the lipid component comprises at least about 5% by weight soybean oil and at least about 50% by weight fatty acids.

17. The composition of claim 11, wherein the secondary solvent comprises a saline solution.

18. The composition of claim 11, wherein the secondary solvent comprises a dextrose solution.

19. The composition of claim 11, wherein the dipolar aprotic solvent or the acid is removed from the composition by lyophilization.

20. A method of preventing or treating an infection in a mammal, comprising the step administering to a mammal a composition as in any one of claims 1, 2, 5, 6, 8, 9, 10, 11, 12, 13, 14, 16, or 17, 19.

* * * * *

UNITED STATES PATENT AND TRADEMARK OFFICE
CERTIFICATE OF CORRECTION

PATENT NO. : 6,844,004 B2
DATED : January 18, 2005
INVENTOR(S) : Borje S. Andersson

It is certified that error appears in the above-identified patent and that said Letters Patent is hereby corrected as shown below:

Column 24,
Line 47, delete "pharmaceutically" and insert -- pharmaceutical -- therefor.
Line 58, after "composition", insert -- is -- therefor.
Line 66, after "comprises", delete "a" therefor.

Column 26,
Lines 20-21, delete "1, 2, 5, 6 ,8, 9, 10, 11, 12, 13, 14, 16, or 17, 19" and insert
-- 1, 2, 3, 4, 5, 6, 7, 8, 9, 10, 11, 12, 13, 14, 15, 16, 17, 18, or 19 -- therefor.

Signed and Sealed this

Twelfth Day of July, 2005

JON W. DUDAS
*Director of the United States Patent and Trademark Office*